(12) United States Patent
Ellsworth et al.

(10) Patent No.: US 7,563,449 B2
(45) Date of Patent: Jul. 21, 2009

(54) METHODS FOR REDUCING CATTLE REPRODUCTIVE DISEASES

(75) Inventors: Michael A. Ellsworth, Lincoln, NE (US); Martin D. Ficken, Bennet, NE (US); Brian J. Fergen, Ames, IA (US); Cassius M. Tucker, Lincoln, NE (US)

(73) Assignee: Pfizer Inc., New York, NY (US)

( * ) Notice: Subject to any disclaimer, the term of this patent is extended or adjusted under 35 U.S.C. 154(b) by 47 days.

(21) Appl. No.: 10/419,661

(22) Filed: Apr. 21, 2003

(65) Prior Publication Data

US 2004/0208901 A1    Oct. 21, 2004

(51) Int. Cl.
| | |
|---|---|
| A61K 39/38 | (2006.01) |
| A61K 39/295 | (2006.01) |
| A61K 39/12 | (2006.01) |
| A61K 39/00 | (2006.01) |
| C12N 7/01 | (2006.01) |
| C12N 7/04 | (2006.01) |
| A61K 39/235 | (2006.01) |

(52) U.S. Cl. ............... 424/229.1; 424/204.1; 424/184.1; 424/201.1; 435/235.1; 435/236

(58) Field of Classification Search ................ None
See application file for complete search history.

(56) References Cited

U.S. PATENT DOCUMENTS

2004/0234506 A1* 11/2004 Jin et al. ................. 424/93.2

FOREIGN PATENT DOCUMENTS

WO    WO 2004/017990 A1 *  3/2004

OTHER PUBLICATIONS

Cravens, R.L. "Efficacy of a temperature-sensitive modified-live bovine herpesvirus type-1 vaccine against abortion and stillbirth in pregnant heifers" J. Am. Vet. Med. Assoc. (Jun. 1996) 208, 12, 2031-2034.*
El Idrissi, A.H. "Comparison of the efficacy of Brucella abortus strain RB51 and Brucella melitensis Rev. 1 live vaccines against experimental infection with Brucella melitensis in pregnant ewes" Rev. Sci. Tech. Off. Int. (2001) 20, 3, 741-747.*
Kacskovics, I "Fc Receptors in livestock species" Vet. Immunol. Immunopathol. (2004) 102, 351-362.*
Bowie, J. U. "Deciphering the Message in Protein Sequences: Tolerance to Amino Acid Substitutions" Science (Mar. 1990) 247, 4948, 1306-1310.*
Muylkens et al., Bovine Herpes 1 infection and infectious bovine rhinotracheitis, Veterinary Research, 2007, vol. 38, pp. 181-209.*
Waldner, Serological status for N. caninum, bovine viral diarrhea virus, and infectious bovine rhinotracheitis virus at pregnancy testing and reproductive performance in beef herds, 2005, Animal Reproductive Science, vol. 90, pp. 219-242.*
Fulton et al., Humoral Immune Response and Assessment of Vaccine Virus Shedding in Calves Receiving Modified Live Virus Vaccines Containing Bovine Herpesvirus-1 and Bovine Viral Diarrhoea Virus 1a, 2003, Journal of Veterinary Medicine, vol. 50, pp. 31-37.*
Parker et al., Experimental Disease-Necrotic Oophoritis in Gilts Associated with Experimental Inoculation of a Viral Gene-deletion Mutant Pseudorabies Vaccine, 1997, Veterinary Pathology, vol. 34, pp. 199-203.*
Anonymous, "Invest early in CattleMaster 4 vaccine to get the highest return", Internet Article, Online URL:wwwpfizer.com/ah/livestock/beef/11_beef.html pp. 1-2, (2002), XP002261912.
Talens L. T. et al., "Efficacy of viral components of a nonabortigenic combination vaccine for prevention of respiratory and reproductive system diseases in cattle", *JAVMA* 194(9): 1273-1280 (1989), XP000568596.
Cortese V. S. et al., "Protection of pregnant cattle and their fetuses against infection with bovine viral diarrhea virus type 1 by use of a modified-live virus vaccine", *AJVR* 59(11): 1409-1413 (1998), XP009037161.
Frey H. R. et al., "Foetal Protection against Bovine Virus Diarrhoea Virus after Two-step Vaccination", *J. Vet. Med. B 49*: 489-493 (2002), XP002297814.
Atkins G., "Vaccination program that work: Alberta Dairy Management", Internet Article, Online URL:www.afns.ualberta.ca/Hosted/DRTC/Articles/Vaccination.asp pp. 1-5 (2004), XP002297700.
Cravens R. L et al., "Efficacy of a temperature-sensitive modified-live bovine herpesvirus type-1 vaccine against abortion and stillbirth in pregnant heifers", *JAVMA* 208(12): 2031-2034 (1996), XP009036969.
Bagley C. V., "Vaccination Program For beef Calves", Internet Article, Online URL:www.extension.usu.edu/files/agpubs/beef40.pdf pp. 1-5 (2004), XP002297701.
Dean H. J. et al., "Cross-protective efficacy of a bovine viral diarrhea virus (BVDV) type 1 vaccine against BVDV type 2 challenge", *Vaccine 17*: 1117-1124 (1999), XP004158233.
Anonymous, "Material safety data sheet: CatttleMaster 4 +VL5", Internet Article, Online URL:www.cattlemastergold.com/pahimages/msds_us/c4.pdf pp. 1-6 (2003), XP002297702.

* cited by examiner

*Primary Examiner*—Bruce Campell
*Assistant Examiner*—Benjamin P Blumel
(74) *Attorney, Agent, or Firm*—Timothy J. Gumbleton

(57) ABSTRACT

The present invention relates to methods for treating or preventing diseases or disorders in a pregnant cow and calf nursing a pregnant cow caused by infection by Bovine Viral Diarrhea Virus (BVDV) Types 1 and 2, Bovine Herpes Virus Type-1 (BHV-1), Bovine Respiratory Syncytial Virus (BRSV), Parainfluenza Virus (PIV3), *Campylobacter fetus, Leptospira canicola, Leptospira grippotyphosa, Leptospira borgpetersenii hardjo-prajitno, Leptospira icterohaemorrhagia, Leptospira hardjo-bovis* and *Leptospira pomona* by administering to the animal an effective amount of a safe modified live viral combination vaccine further combined with a multivalent bacterin vaccine.

9 Claims, No Drawings

METHODS FOR REDUCING CATTLE REPRODUCTIVE DISEASES

FIELD OF THE INVENTION

The present invention relates to methods for safely vaccinating pregnant cows and calves nursing pregnant cows to prevent diseases or disorders, such as abortion caused by infection by Bovine Viral Diarrhea Virus (BVDV) Types 1 and 2, Bovine Herpes Virus Type-1 (BHV-1), Bovine Respiratory Syncytial Virus (BRSV), Parainfluenza Virus Type 3 (PIV$_3$), *Campylobacter fetus*, *Leptospira canicola*, *Leptospira grippotyphosa*, *Leptospira borgpetersenii hardjoprajitno*, *Leptospira icterohaemmorrhagiae*, *Leptospira borgpetersenii hardjo-bovis* and *Leptospira interrogans pomona* by administering to the animal an effective amount of a combination vaccine. The methods of the present invention employ a combination vaccine that can be a whole or partial cell inactivated and/or modified live preparation.

BACKGROUND OF THE INVENTION

Five viral agents associated with the bovine respiratory disease (BRD) complex—Bovine Herpes Virus Type-1 (BHV-1), also known as Infectious Bovine Rhinotracheitis Virus (IBRV), Bovine Viral Diarrhea Virus (BVDV) Types 1 and 2, Bovine Respiratory Syncytial Virus (BRSV), and Parainfluenza Virus Type 3 (PIV$_3$), cause respiratory and reproductive system infections of great economic importance to the beef and dairy industries worldwide. BRD causes a broad array of clinical syndromes including acute onset respiratory disease and abortion. The respiratory form of BRD is characterized by inflammation, swelling, hemorrhage, and necrosis of the mucous membranes of the respiratory tract and may be accompanied by high fever, anorexia, depression, nasal discharge, labored breathing, and inflamed muzzle. Abortions induced by IBRV and BVDV virus can occur in all three trimesters, but chiefly during the last half of gestation, and often without evidence of other clinical signs (Ellis et al. (1996) *JAVMA* 208:393-400; Ellsworth et al. (1994) In: Proceedings, 74$^{th}$ Conference of Research Workers in Animal Disease:34).

Bovine Herpes Virus Type-1 (BHV-1), is a member of the alphaherpesviridae subfamily, and produces a variety of clinical forms of disease in cattle, including respiratory and genital infections, conjunctivitis, encephalitis, and abortions. Previous attempts at controlling BHV-1 infection have utilized vaccines comprising live attenuated virus (Gerber, J. D., et al., 1978, Am. J. Vet. Res. 39:753-760; Mitchell, D., 1974, Can. Vet. Jour. 15:148-151), inactivated virus (Frerichs, G. N., et al., 1982, Vet. Rec. 111:116-122), and viral subunits such as, e.g., one of the three major BHV-1 glycoproteins, which have been designated in the art as gI, gIII, and gIV (Babiuk, L. A., et al., 1987, Virology 159:57-66; van Drunen, S., et al., 1993, Vaccine 11:25-35). In addition, the ability of a recombinant, truncated version of the BHV-1 gIV glycoprotein (designated in the art as BHV-1 tgIV) to induce mucosal immunity against BHV-1 has been demonstrated (van Drunen, S., et al., 1994, Vaccine, 12:1295-1302). However, the art-recognized modified-live BHV-1 vaccines are contraindicated for use in pregnant cattle, seropositive or seronegative, and also contraindicated for use in calves nursing pregnant cows.

BVDV types 1 and 2 have been implicated in a variety of clinical syndromes. Studies have established that the virus causes severe primary respiratory disease; that persistently infected (PI) cattle are a major source of infection for susceptible calves; and that BVDV infects white cell reservoirs, causing profound and broad-based deficits in the immune system. Ellis et al. (1996) JAVMA 208:393-400; Baum et al. (1993) The Compendium Collection: Infectious Disease in Food Animal Practice. Trenton, N.J. Veterinary Learning Systems-1 13-121; Meyling et al. (1987) Agric Pestivirus Infect Rumin 225-231. Abortion or mummification can result when pregnant cattle become infected especially during the first trimester. Bolin et al. (1989) Am J. Vet Res 52:1033-1037. Mucosal disease, another often fatal manifestation of bovine viral diarrhea (BVD), results from early fetal infection with a noncytopathic BVDV biotype, development of immunotolerance to the virus, birth of a persistently infected (PI) calf, and subsequent superinfection with a cytopathic BVDV biotype. Bolin et al. (1989) Am J. Vet Res 52:1033-1037. BVDV type 2, once recognized chiefly as a hemorrhagic BVDV isolate mostly in dairy herds, has become the predominant strain isolated in most regions of the United States from both BVDV-related abortions and respiratory cases. Van Oirschot et al. (1999) Vet Micro 64:169-183.

BVDV is classified in the pestivirus genus and Flaviviridae family. It is closely related to viruses causing border disease in sheep and classical swine fever. Infected cattle exhibit "mucosal disease" which is characterized by elevated temperature, diarrhea, coughing and ulcerations of the alimentary mucosa (Olafson, et al., Cornell Vet. 36:205-213 (1946); Ramsey, et al., North Am. Vet. 34:629-633 (1953)). The BVD virus is capable of crossing the placenta of pregnant cattle and may result in the birth of Pi calves (Malmquist, J. Am. Vet. Med. Assoc. 152:763-768 (1968); Ross, et al., J. Am. Vet. Med. Assoc. 188:618-619 (1986)). These calves are immunotolerant to the virus and persistently viremic for the rest of their lives. They provide a potential source for outbreaks of mucosal disease (Liess, et al., Dtsch. Tieraerztl. Wschr. 81:481-487 (1974) and are highly predisposed to infection with microorganisms causing diseases such as pneumonia or enteric disease (Barber, et al., Vet. Rec. 117:459-464 (1985).

According to BVDV virus growth studies in cultured cells, two viral biotypes have been classified: viruses that induce a cytopathic effect (cp) and viruses that do not induce a cytopathic effect (ncp) in infected cells (Lee et al., Am. J. Vet. Res. 18: 952-953; Gillespie et al., Cornell Vet. 50: 73-79, 1960). Cp variants can arise from the PI animals preinfected with ncp viruses (Howard et al., Vet. Microbiol. 13: 361-369, 1987; Corapi et al., J. Virol. 62: 2823-2827, 1988). Based on the genetic diversity of the 5' non-translated-region (NTR) and the antigenic differences in the virion surface glycoprotein E2 of BVD viruses, two major genotypes have been proposed: type 1 and 2. BVDV type 1 represents classical or traditional virus strains which usually produce only mild diarrhea in immunocompetent animals, whereas BVDV type 2 are emerging viruses with high virulence which can produce thrombocytopenia, hemorrhages and acute fatal disease (Corapi et al., J. Virol. 63: 3934-3943; Bolin et al., Am. J. Vet. Res. 53: 2157-2163; Pellerin et al., Virology 203: 260-268, 1994; Ridpath et al., Virology 205: 66-74, 1994; Carman et al., J. Vet. Diagn. Invest. 10: 27-35, 1998). Type 1 and 2 BVDV viruses have distinct antigenicity determined by a panel of monoclonal antibodies (Mabs)and by cross-neutralization using virus-specific antisera raised in animals (Corapi et al., Am. J. Vet. Res. 51: 1388-1394, 1990). Viruses of either genotype may exist as one of the two biotypes, cp or ncp virus.

Studies from BVD virus infected animals suggest that BVD viruses induce both B-cell and T-cell responses in animals (Donis et al., Virology 158: 168-173, 1987; Larsson et al., Vet. Microbiol. 31: 317-325, 1992; Howard et al., Vet.

Immunol. Immunopathol. 32: 303-314, 1992; Lambot et al., J. Gen. Virol. 78: 1041-1047,1997; Beer et al., Vet. Microbiology. 58: 9-22, 1997).

A number of BVDV vaccines have been developed using chemically inactivated BVD viral isolates (Fernelius et al., Am. J. Vet. Res. 33: 1421-1431, 1972; Kolar et al., Am. J. Vet. Res. 33: 1415-1420, 1972; McClurkin et al., Arch. Virol. 58: 119, 1978). Multiple doses are required for the inactivated viral vaccines to achieve primary immunization. Some inactivated BVDV vaccines provide protection against infection by type I BVDV only (Beer et al., Vet. Microbiology. 77:195-208, 2000). Fetal protection has not been achieved with inactivated BVDV vaccines due to a short duration of immunity and an inefficient cross-type protection (Bolin, Vet. Clin. North Am. Food Anim. Pract. 11: 615-625, 1995).

Modified-live virus (MLV) vaccines, on the other hand, offer a higher level of protection. Currently, licensed BVDV MLV vaccines are produced using attenuated viruses obtained via repeated passage in cell culture (Coggins et al., Cornell Vet. 51: 539-, 1961; Phillips et al., Am. J. Vet. Res. 36: 135-, 1975), or using chemically modified viruses which exhibit a temperature-sensitive phenotype (Lobmann et al., Am. J. Vet. Res. 45: 2498-, 1984; 47: 557-561, 1986). A single dose of MLV vaccine is sufficient for immunization, and duration of the immunity can last for years in vaccinated cattle. However, as these vaccines have been developed using type I BVDV virus strains, maximum protection is against type I virus. Moreover, the available modified-live BVDV vaccines are not indicated for use in pregnant cattle or calves nursing pregnant cows.

PIV3 virus typically produces only mild disease when acting alone; however, the virus predisposes the respiratory tract to secondary infection with more pathogenic organisms including IBRV virus, BRSV, and BVDV, resulting in the classic shipping fever syndrome. Of the various viruses known to cause respiratory disease in cattle, PIV3 virus is the most widespread. Ellis et al. (1996) JAVMA 208:393-400.

BRSV has a preference for the lower respiratory tract, and severity of infection is determined chiefly by the immune system's response to key viral proteins. Bolin et al. (1990) Am J Vet Res 51:703. Affected cattle generally show nonspecific signs including serous nasal and ocular discharge, a mild, often biphasic fever, and dry, hacking cough. More severely affected cattle develop a harsh cough, show labored, open-mouth breathing, and frothy saliva around the mouth, and may quit eating and drinking. Ellis et al. (1996) JAVMA 208:393-400.

Leptospirosis, caused by spirochetes of the genus *Leptospira*, is an economically important zoonotic infection of livestock. *Leptospira borgpetersenii serovar hardjo* (*L. hardjo*) and *L. interrogans serovar pomona* (*L. pomona*) are the two serovars most commonly associated with cattle leptosporosis worldwide. In one survey of US cattle, 29% reacted serologically with *L. hardjo*, and 23% with *L. pomona*. Leptospires invade the body via mucous membranes or broken skin, and are disseminated via the blood. They display tropisms for the kidney and genital tract, and less commonly the vitreous humor of the eye and the central nervous system. The most common means of infection is by direct or indirect contact with infected urine, milk, or placental fluids, but venereal and trans-ovarian transmission are also known. Leptospiral infection of cattle may result in acute fever, agalactia, abortion, or birth of premature and weak infected calves, and may contribute to breeding failures and low conception rates. Infections can be treated with antibiotics, but they may be inapparent in cattle that are not lactating or pregnant. In such cattle they establish acute or chronic infection of the kidneys, resulting in urinary shedding of virulent organisms which in turn may infect other animals or their human handlers. Immunity to Leptospira is serovar specific, and although vaccines have been available for many years, most induce only a poor and short-lived immunity.

There is therefore a need for methods for safely vaccinating pregnant cattle and protecting pregnant cattle from transmission after vaccination from their nursing offspring against a large variety of antigens. There is also a need for the treatment and prevention of the major infectious causes of respiratory and reproductive disease in animals, such as cows and calves.

SUMMARY OF THE INVENTION

The present invention provides a method of treating or preventing a disease or disorder in an animal caused by infection with at least one of BVDV Type 1 or Type 2, BHV-1, $PIV_3$, BRSV, *Campylobacter fetus, Leptospira canicola, Leptospira grippotyphosa, Leptospira borgpetersenii hardjo-prajitno, Leptospira icterohaemmorrhagiae, Leptospira borgpetersenii hardjo-bovis* and *Leptospira interrogans pomona* comprising administering to the animal, an effective amount of a combination vaccine.

The present method provides protection to animals such as bovine, in particular, against systemic infection and reproductive disease. The present method provides protection to animals such as pregnant cows against abortion caused by BHV-1 (IBRV) and BVDV and persistent fetal infections caused by BVDV types 1 and 2. The present method also provides protection to animals such as lactating cows and calves nursing pregnant cows against infections caused by BVDV types 1 and 2. The present method also provides protection to breeding age animals, pregnant animals and lactating animals. Thus, the present method provides protection to animals prior to breeding and during gestation. The present method further provides protection to animals with a history of annual vaccinations against infection or disease caused by IBRV, BVDV, PIV3, BRSV, *Campylobacter fetus* and/or *Leptospirae*.

The combination vaccine employed in the present methods can be a whole or partial cell preparation and/or modified live preparation. The monovalent or combination vaccine administered in accordance with the present invention may include additional components, such as an adjuvant and optionally a second or more antigens. A second antigen is selected from the following, including, but not limited, to bovine herpesvirus type 1 (BHV-1), bovine viral diarrhea virus (BVDV type 1 or 2), bovine respiratory syncitial virus (BRSV), parainfluenza type 3 virus ($PIV_3$), *Leptospira canicola, Leptospira grippotyphosa, Leptospira borgpetersenii hardjo-prajitno, Leptospira icterohaemmorrhagia, Leptospira interrogans pomona, Leptospira borgpetersenii hardjo-bovis, Leptospira bratislava,* and *Campylobacter fetus*.

DETAILED DESCRIPTION OF THE INVENTION

The present invention provides a method of treating or preventing a disease or disorder in an animal caused by infection with IBRV, BVDV, $PIV_3$, BRSV, *Campylobacter fetus* and/or *Leptospirae* by administering to the animal, an effective amount of a combination vaccine In one embodiment, the present invention provides methods for vaccinating pregnant cows and calves nursing pregnant cows to prevent systemic diseases or disorders such as abortion caused by infection by IBRV, BVDV, $PIV_3$, BRSV, *Campylobacter fetus* and/or *Leptospirae*.

In certain embodiments, the vaccines used in the method of the present invention comprise a modified live vaccine and a pharmaceutically acceptable carrier, or a modified live vaccine and an adjuvant.

For clarity of disclosure, and not by way of limitation, the detailed description of the invention is divided into the following subsections which describe or illustrate certain features, embodiments or applications of the invention.

Definitions and Abbreviations

The term "treating or preventing" with respect to a disease or disorder as used herein means reducing or eliminating the risk of infection by a virulent BVDV types 1 and 2; IBRV; $PIV_3$; BRSV; *Campylobacteria;* and/or *Leptospira* antigens, ameliorating or alleviating the symptoms of an infection, or accelerating the recovery from an infection. The treatment is considered therapeutic if there is a reduction in viral or bacterial load, decrease in pulmonary infections, reduced rectal temperatures, and/or increase in food uptake and/or growth. The treatment is also considered therapeutic if there is a reduction in fetal infection and urinary shedding due to infection with *Leptospira serovars hardjo* and *pomona,* for example. By "infection" is meant a systemic manifestation of symptoms including but not limited to increased rectal temperatures, decreased food uptake and/or growth. Infection is also understood to include respiratory, intestinal, pulmonary and reproductive subtypes.

The method of the present invention is, for example, effective in preventing or reducing abortion caused by IBRV and infections caused by BVDV types 1 and 2, and reducing rectal temperatures. The present invention is therefore contemplated to provide fetal protection against BHV-1 (IBRV) and infections caused by BVDV types 1 and 2 as well as fetal protection against cattle herpes and cattle pestiviruses. The present invention is also contemplated to provide protection against persistent fetal infection, such as persistent BVDV infection. By "persistent fetal infection" is meant infection occurring during early fetal development (e.g., 45-125 days of gestation) that leads to the live birth of animals that are immunotolerant to BVDV and maintain active BVDV replication and multiplication that often occurs at a high rate for months or years, serving as a permanent source of BVDV in the herd. These persistently infected animals are also at risk of developing fatal mucosal disease if superinfected with a cytopathic virus biotype.

The term "combination vaccine" is meant a bivalent or multivalent combination of antigens including modified live antigens. In accordance with the present invention a combination vaccine can comprise modified live infectious IBRV, $PIV_3$, BRSV and BVDV types 1 and 2, one or more antigens such as but not limited to *Leptospira canicola, Leptospira grippotyphosa, Leptospira borgpetersenii hardio-prajitno, Leptospira icterohaemmorrhagia, Leptospira interrogans pomona, Leptospira borgpetersenii hardjo-bovis, Leptospira bratislava,* and *Campylobacter fetus,* a veterinary acceptable carrier and an adjuvant. In one embodiment the modified live IBRV component is not a temperature sensitive IBRVV. In a preferred embodiment the BVDV type 1 component is cytopathic (cpBVD-1 strain NADL-National Animal Disease Center, United States, Dep. of Agriculture, Ames, Iowa). In another preferred embodiment the BVDV type 2 component is modified live cytopathic (cp BVD-2 strain 53637, ATCC No. PTA-4859). In another preferred embodiment, the modified live antigens are desiccated, lyophilized or vitrified.

In accordance with the present invention a combination vaccine can comprise modified live BHV-1, BVDV types 1 and 2, one or more antigens such as, but not limited to, BRSV, PIV3, *Leptospira canicola, Leptospira grippotyphosa, Leptospira borgpetersenii hardio-prajitno, Leptospira icterohaemmorrhagia, Leptospira interrogans pomona, Leptospira borgpetersenii hardjo-bovis, Leptospira bratislava,* and *Campylobacter fetus,* a veterinary acceptable carrier and an optional adjuvant. The term "combination vaccine" as used herein also refers to a multicomponent composition containing at least one modified live antigen, at least one second antigen and an adjuvant (adjuvant is optional) which prevents or reduces the risk of infection and/or which ameliorates the symptoms of infection. In a preferred embodiment the source of the combination vaccine is Bovi-Shield® FPT™ 4+VL5 or Bovi-Shield® FP™5 (Pfizer, Inc.)

The protective effects of a combination vaccine composition against a pathogen are normally achieved by inducing in the subject an immune response, either a cell-mediated or a humoral immune response or a combination of both. Generally speaking, abolished or reduced incidences of BVDV, IBRV, and/or PIV3 infection, amelioration of the symptoms, or accelerated elimination of the viruses from the infected subjects are indicative of the protective effects of a combination vaccine composition. The methods of the present invention provide protection against infections caused by either or both type 1 and type 2 BVD viruses as well as infection or abortions caused by BHV-1 (IBRV) and respiratory infections caused by PIV3 and BRSV.

The present method of treating or preventing a disease or disorder in an animal caused by infection with IBRV, BVDV, PIV3, BRSV, *Campylobacter fetus* and/or *Leptospirae* by administering a combination vaccine is also referred to herein as a vaccination method.

The term "combination vaccine" that may be used in the present methods can include, for example, an inactivated whole or partial *C. fetus* and/or *Leptospira* cell preparation, modified live BVDV types 1 and 2 and/or one or more modified live antigens such as BHV-1, PIV3 and/or BRSV.

In one embodiment, the vaccine compositions of the present invention include an effective amount of one or more of the above-described BVDV viruses, preferably cpBVD-1 strain NADL (cpBDV-1 strain NADL-National Animal Disease Center, United States Department of Agriculture, Ames, Iowa); cpBVD-2 strain 53637 (ATCC No. PTA4859), IBRV strain C-13 (Cutter Laboratories); PIV3 strain Reisinger (Univ. Nebraska); BRSV strain 375 (Veterinary Medical Research Institute, Ames, Iowa) Purified BVDV viruses can be used directly in a vaccine composition, or preferably, BVD viruses can be further modified by way of serial passages in vitro. Typically, a vaccine contains between about $1\times10^2$ and about $1\times10^{10}$ plaque forming or $TCID_{50}$ units of virus, with a veterinary acceptable carrier and optionally an adjuvant, in a volume of between 0.1 and 5 ml and preferably about 2 ml. The precise amount of a virus in a vaccine composition effective to provide a protective effect can be determined by a skilled veterinary physician. Veterinary acceptable carriers suitable for use in vaccine compositions can be any of those described hereinbelow.

In another embodiment, the vaccine compositions of the present invention include an effective amount of one or more of the above-described BHV-1 (IBRV) viruses, preferably IBRV strain C-13 (Cutter Laboratories); Typically, a vaccine contains between about $1\times10^2$ and about $1\times10^{10}$ plaque or colony forming units of virus, with a veterinary acceptable carrier and an adjuvant, in a volume of between 0.1 and 5 ml and preferably about 2 ml. The precise amount of a virus in a vaccine composition effective to provide a protective effect can be determined by a skilled veterinary physician. Veterinary acceptable carriers suitable for use in vaccine compositions can be any of those described hereinbelow. The typical route of administration will be intramuscular or subcutaneous injection of between about 0.1 and about 5 ml of vaccine. The vaccine compositions of the present invention can also include additional active ingredients such as other vaccine compositions against BVDV, e.g., those described in WO 95/12682, WO 99/55366, U.S. Pat. Nos. 6,060,457, 6,015, 795, 6,001,613, and 5,593,873.

Vaccination can be accomplished by a single inoculation or through multiple inoculations. If desired, sera can be collected from the inoculated animals and tested for the presence of antibodies to BVD virus and IBRV virus.

In another embodiment of the present invention, the vaccine compositions are used in treating BVDV infections. Accordingly, the present invention provides methods of treating infections in animal subjects caused by BVD viruses of type 1 or type 2, or a combination of type 1 and type 2, by administering to an animal, a therapeutically effective amount of a BVD virus of the present invention. In another embodiment the vaccine compositions of the present invention are effective for the improvement of herd fertility, and for the reduction of the risk of disease transmission from cattle to human handlers.

By "animal subject" is meant to include any animal that is susceptible to BVDV, BHV, PIV3, BRSV or *Leptospira* infections, for example, such as bovine, sheep and swine. In one embodiment, the animal subject is a cow, calf or heifer. In a preferred embodiment, the animal subject is a lactating cow. In another preferred embodiment, the animal subject is a prebreeding cow, a pregnant cow or a calf nursing a pregnant cow.

In practicing the present methods, a vaccine composition of the present invention is administered to cattle preferably via intramuscular or subcutaneous routes, although other routes of administration can be used as well, such as e.g., by oral, intranasal (e.g. aerosol or other needleless administration), intra-lymph node, intradermal, intraperitoneal, rectal or vaginal administration, or by a combination of routes. Intramuscular administration in the neck region of the animal is preferred. Boosting regimens may be required and the dosage regimen can be adjusted to provide optimal immunization.

By "immunogenic" is meant the capacity of a BVD virus to provoke an immune response in an animal against type 1 or type 2 BVD viruses, or against both type 1 and type 2 BVD viruses. The immune response can be a cellular immune response mediated primarily by cytotoxic T-cells, or a humoral immune response mediated primarily by helper T-cells, which in turn activates B-cells leading to antibody production.

According to the present invention, the viruses are preferably attenuated by serial passages in cell culture prior to use in an immunogenic composition. The methods of modification are well known to those skilled in the art.

A preferred virus to be included in an immunogenic composition in the methods of the present invention is BVDV cpBVDV NADL (Type 1). Another preferred virus to be included in an immunogenic composition of the present invention is cp53637(ATCC No. PTA-4859). A further preferred virus to be included in an immunogenic composition of the present invention is IBRV strain C-13. Another preferred virus to be included in an immunogenic composition of the present inventions is PIV3 strain Reisinger. Yet another preferred virus to be included in an immunogenic composition of the present invention is BRSV strain 375.

The immunogenic compositions used in the methods of the present invention can also include additional active ingredients such as other immunogenic compositions against BVDV, e.g., those described in copending application Ser. No. 08/107,908, WO 95/12682, WO 99/55366, U.S. Pat. Nos. 6,060,457, 6,015,795, 6,001,613, and 5,593,873.

In addition, the immunogenic and vaccine compositions employed in the methods of the present invention can include one or more veterinary-acceptable carriers. As used herein, "a veterinary-acceptable carrier" includes any and all solvents, dispersion media, coatings, adjuvants, stabilizing agents, diluents, preservatives, antibacterial and antifungal agents, isotonic agents, adsorption delaying agents, and the like. Diluents can include water, saline, dextrose, ethanol, glycerol, and the like. Isotonic agents can include sodium chloride, dextrose, mannitol, sorbitol, and lactose, among others. Stabilizers include albumin, among others. Adjuvants include, but are not limited to, the RIBI adjuvant system (Ribi Inc.), alum, aluminum hydroxide gel, Cholesterol, oil-in water emulsions, water-in-oil emulsions such as, e.g., Freund's complete and incomplete adjuvants, Block co-polymer (CytRx, Atlanta Ga.), SAF-M (Chiron, Emeryville Calif.), AMPHIGEN® adjuvant, saponin, Quil A, QS-21 (Cambridge Biotech Inc., Cambridge Mass.), GPI-0100 (Galenica Pharmaceuticals, Inc., Birmingham, Ala.) or other saponin fractions, monophosphoryl lipid A, Avridine lipid-amine adjuvant, heat-labile enterotoxin from *E. coli* (recombinant or otherwise), cholera toxin, or muramyl dipeptide, among many others. The immunogenic compositions can further include one or more other immunomodulatory agents such as, e.g., interleukins, interferons, or other cytokines. The immunogenic compositions employed in the methods of the present invention can also include Gentamicin and Merthiolate. While the amounts and concentrations of adjuvants and additives useful in the context of the present invention can readily be determined by the skilled artisan, the present invention contemplates compositions comprising from about 50 ug to about 2000 ug of adjuvant and preferably about 500 ug/2 ml dose of the vaccine composition. In another preferred embodiment, the present invention contemplates vaccine compositions comprising from about 1 ug/ml to about 60 ug/ml of antibiotic, and more preferably less than about 30 ug/ml of antibiotic.

The immunogenic compositions employed in the methods of the present invention can be made in various forms depending upon the route of administration. For example, the immunogenic compositions can be made in the form of sterile aqueous solutions or dispersions suitable for injectable use, or made in lyophilized forms using freeze-drying techniques. Lyophilized immunogenic compositions are typically maintained at about 4° C., and can be reconstituted in a stabilizing solution, e.g., saline or and HEPES, with or without adjuvant.

The immunogenic compositions of the present invention can be administered to animal subjects to induce an immune response against type 1 or type 2 BVD viruses, or against both type 1 and type 2 BVD viruses. Accordingly, another embodiment of the present invention provides methods of stimulating an immune response against type 1 or type 2 BVD viruses, or against a combination of type 1 and type 2 BVD viruses by administering to an animal subject an effective amount of an immunogenic composition of the present invention described above. By "animal subject" is meant to include any animal that is susceptible to BVDV infections, such as bovine, sheep and swine.

In accordance with the methods of the present invention, a preferred immunogenic composition for administration to an animal subject includes the BVDV cpNADL virus and/or the BVDV cp53637 virus. An immunogenic composition containing a BVDV virus, preferably modified live by serial passage in culture, is administered to a cattle preferably via intramuscular or subcutaneous routes, although other routes of administration can be used as well, such as e.g., by oral, intranasal, intra-lymph node, intradermal, intraperitoneal, rectal or vaginal administration, or by a combination of routes.

Immunization protocols can be optimized using procedures well known in the art. A single dose can be administered to animals, or, alternatively, two or more inoculations can take place with intervals of two to ten weeks. Depending on the age of the animal, the immunogenic or vaccine composition can be readministered. For example, the present invention contemplates the vaccination of healthy cattle prior to six months of age and revaccination at six months of age. In another example, the present invention contemplates the vaccination of prebreeding cattle at about 5 weeks prebreeding (or prior to being added to a herd) and optionally again at about 2 weeks prebreeding or during gestation to protect a fetus against infection caused by BVDV Types 1 and 2. Single doses of the compositions of the present invention can also be administered about 3 to 4 weeks after a first dose. Semiannual revaccination with a single dose of the combination vaccine is also contemplated to prevent BVDV fetal infection.

The extent and nature of the immune responses induced in the cattle can be assessed by using a variety of techniques. For example, sera can be collected from the inoculated animals and tested for the presence of antibodies specific for BVDV viruses, e.g., in a conventional virus neutralization assay.

The term "cattle" as used herein refers to bovine animals including but not limited to steer, bulls, heifers, cows, and calves. Cattle as used herein refers to pregnant and lactating bovine animals. Preferably, the method of the present invention is applied to an animal which is a non-human mammal; preferably, a lactating or pregnant cow and its fetus, or a nursing calf.

The term "therapeutically effective amount" or "effective amount" refers to an amount of combination vaccine sufficient to elicit an immune response in the animal to which it is administered. The immune response may comprise, without limitation, induction of cellular and/or humoral immunity. The amount of a vaccine that is therapeutically effective may vary depending on the particular virus used, the condition of the cattle and/or the degree of infection, and can be determined by a veterinary physician.

Inactivated (Partial or Whole Cell) and Modified Live Vaccines

Inactivated or modified live vaccines for use in the method of the present invention can be prepared using a variety of methods which are known in the art.

For example, BVDV isolates can be obtained directly from infected cow uteri using known techniques.

BVDV isolates can be attenuated using a variety of known methods including serial passage, for example. In addition to modified live viral isolates, a vaccine product employed in the methods of the present invention can also include an appropriate amount of one or more commonly used adjuvants. Suitable adjuvants may include, but are not limited to: mineral gels, e.g., aluminum hydroxide; surface active substances such as lysolecithin; glycosides, e.g., saponin derivatives such as Quil A or GPI-0100; pluronic polyols; polyanions; non-ionic block polymers, e.g., Pluronic F-127 (B.A.S.F., USA); peptides; mineral oils, e.g. Montanide ISA-50 (Seppic, Paris, France), carbopol, Amphigen, Amphigen Mark II (Hydronics, USA), Alhydrogel, oil emulsions, e.g. an emulsion of mineral oil such as BayolF/Arlacel A and water, or an emulsion of vegetable oil, water and an emulsifier such as lecithin; alum; bovine cytokines; cholesterol; and combinations of adjuvants. In a preferred embodiment, the saponin containing oil-in-water emulsion is conventionally microfluidized.

A particularly preferred source of BVDV type 1, for use in the method of the present invention is Bovi-Shield® FP™ 4+VL5 (PFIZER INC.), containing BVDV strain NADL (acquired from the National Animal Disease Center (NADC), USDA, Ames, Iowa). A preferred source of BVDV Type 2 for use in the methods of the present invention is cp BVDV strain 53637 (Univ. Guelph, Guelph, Ont.) (ATCC No. PTA-4859).

Preferably, the strains NADL and 53637 are modified live strains. In accordance with the present invention, the strains of the present invention can be adjuvanted with a commercially available adjuvant, preferably, Quil A-Cholesterol-Amphigen (Hydronics, USA). A preferred dose of the immunogenic and vaccine compositions of the present invention is about 2.0 ml. Preservatives can be included in the compositions employed in the methods of the present invention. Preservatives contemplated by the present invention include gentamicin and merthiolate. A carrier can also be added, preferably, PBS. Preparation of modified live vaccines, such as by attenuation of virulent strains by passage in culture, is known in the art.

Modified live BVDV isolates can also be combined with the following bacteria and viruses, including but not limited to, bovine herpesvirus type 1 (BHV-1), bovine respiratory syncitial virus (BRSV), parainfluenza virus (PIV3), *Campylobacter fetus, Leptospira canicola, Leptospira grippotyphosa, Leptospira borgpetersenii hardjo-prajitno, Leptospira icterohaemmorrhagiae, Leptospira borgpetersenii hardlo-bovis* and *Leptospira interrogans pomona*.

Dosing and Modes of Administration

According to the present invention, an effective amount of a combination vaccine administered to cattle, including pregnant cows and calves nursing pregnant cows provides effective immunity against disease and fetal infection associated with BHV-1 and Bovine Viral Diarrhea Virus (Type 1 and 2). In one embodiment, the combination vaccine is administered to calves in two doses at an interval of about 3 to 4 weeks. For example, the first administration is performed when the animal is about 1 to about 3 months of age. The second administration is performed about 1 to about 4 weeks after the first administration of the combination vaccine.

In a preferred embodiment, the first administration, e.g. pre-vaccination, is performed about 4 to 5 weeks prior to animal breeding. The second administration is performed about 3 to 4 weeks after animal breeding. Administration of subsequent vaccine doses is preferably done on an annual basis. In another preferred embodiment, animals vaccinated before the age of about 6 months should be revaccinated after 6 months of age. Administration of subsequent vaccine doses is preferably done on an annual basis, although bi-annual and semi-annual subsequent vaccine doses are also contemplated by the present invention.

The amount of combination vaccine that is effective depends on the ingredients of the vaccine and the schedule of administration. Typically, when a modified live Bovine Viral Diarrhea Virus preparation is used in a vaccine, an amount of the vaccine containing about $10^2$ to about $10^{10}$ TCID$_{50}$ units per dose of BVDV, and preferably about $10^5$ to about $10^8$ TCID$_{50}$ units per dose of BVDV (Type 1 and 2) is effective when administered twice to the animal during a period of about 3 to 10 weeks. Preferably, a combination vaccine that provides effective immunity contains about $10^5$ to $10^8$ TCID$_{50}$ units/dose of BVDV (Type 1 and 2) and more preferably, about $10^6$ TCID$_{50}$ units/dose, when administered twice to the animal during a period of about 3 to 10 weeks. The first administration is performed about 5 weeks prior to animal breeding. The second administration is performed about 3 to 4 weeks after animal breeding. Administration of subsequent vaccine doses is preferably done on an annual basis. Animals vaccinated before the age of about 6 months should be revaccinated after 6 months of age. Administration of subsequent vaccine doses is preferably done on an annual basis.

According to the present invention, when the preferred product, Bovi-Shield® FP™ 4+VL5 (Pfizer, Inc.), is administered, the product is administered preferably twice, each time in the amount of about 0.1 ml to about 5.0 ml, preferably about 1.5 ml to about 2.5 ml, and more preferably, about 2 ml. The first administration is performed about 5 weeks prior to animal breeding. The second administration is performed about 3 to 4 weeks after animal breeding. Administration of subsequent vaccine doses is preferably done on an annual basis. Animals vaccinated before the age of about 6 months should be revaccinated after 6 months of age. Administration of subsequent vaccine doses is preferably done on an annual basis.

In accordance with the present invention, administration can be achieved by known routes, including the oral, intranasal, topical, transdermal, and parenteral (e.g., intravenous, intraperitoneal, intradermal, subcutaneous or intramuscular). A preferred route of administration is subcutaneous or intramuscular administration.

The present invention also contemplates a single primary dose followed by annual revaccination, which eliminates the necessity of administration of additional doses to calves prior to annual revaccination in order to generate and/or maintain immunity against infection.

The combination vaccine administered in accordance with the present invention can include additional components, such as an adjuvant (e.g., mineral gels, e.g., aluminum hydroxide; surface active substances such as Cholesterol, lysolecithin; glycosides, e.g., saponin derivatives such as Quil A, QS-21 or GPI-0100; pluronic polyols; polyanions; non-ionic block polymers, e.g., Pluronic F-127; peptides; mineral oils, e.g. Montanide ISA-50, carbopol, Amphigen®, Alhydrogel, oil emulsions, e.g. an emulsion of mineral oil such as BayolF/Arlacel A and water, or an emulsion of vegetable oil, water and an emulsifier such as lecithin; alum; bovine cytokines; and combinations of adjuvants.).

According to the present invention, the administration of an, effective amount of a combination vaccine administered to cattle at approximately 3 months of age provides effective immunity against respiratory infections and reproductive disease, and reduces abortions.

The present invention also provides a method of immunizing cattle, including but not limited to cows, calves, and prebreeding heifers, against infection and abortion caused by BHV-1 and BVDV (types 1 and 2), and respiratory disease attributed to IBRV, BVDV (Types 1 and 2), PJV3, BRSV, campylobacteriosis and leptospiriosis by administering to the animal at least one dose, and preferably two doses of the combination vaccine in order to immunize the animal against infection caused by BVD (types 1 and 2), IBRV, PIV3, BRSV, *Leptospira canicola, Leptospira grippotyphosa, Leptospira borgpetersenii hardio-prajitno, Leptospira icterohaemorrhagia, Leptospira interrogans pomona, Leptospira borgpetersenii hardjo-bovis, Leptospira bratislava,* and *Campylobacter fetus.*

In a preferred embodiment, the vaccine is administered subcutaneously. In another preferred embodiment, the vaccine is administered intramuscularly. Moreover, it is preferred that the vaccine dose comprise about 1 ml to about 7 ml, and preferably about 2 ml, each ml containing about $10^2$ to about $10^{10}$ TCID$_{50}$ units/per dose of virus. The combination vaccine is desirably administered twice to the animal; once at about 1 to about 3 months of age, and once at about 1 to 5 weeks later. The present invention also contemplates semiannual revaccinations with a single dose and revaccination prior to breeding.

The present invention also provides a method of protecting bovine fetuses against fetal infection and persistent fetal infection, comprising administering to the animal (e.g. dam) at least one dose, and preferably two doses of the combination vaccine in order to immunize the fetus against infection caused by BVD (types 1 and 2), IBRV, PIV3, BRSV, *Leptospira canicola, Leptospira grippotyphosa, Leptospira borgpetersenii hardio-prajitno, Leptospira icterohaemorrhagia Leptospira interrogans pomona, Leptospira borgpetersenii hardjo-bovis, Leptospira bratislava,* and *Campylobacter fetus.* The combination vaccine is desirably administered twice to the animal, once about five weeks prior to breeding and once at about three to four weeks after breeding.

The present invention also contemplates that the administration of an effective amount of a combination vaccine administered to animals, and preferably cattle to treat or prevent disorders including persistent fetal infections and reproductive disorders, such as abortions in such animals.

The present invention is further illustrated, but not limited by the following examples.

EXAMPLE 1

An intensive safety study was conducted to evaluate the safety for administering a Bovine Rhinotracheitis-Virus Diarrhea-Parainfluenza$_3$-Respiratory Syncytial Modified-Live Virus Vaccine/Leptospira Canicola-Grippotyphosa-Hardjo-Icterohemorrhagia-Pomona Bacterin (Bovi-Shield® 4+L5) formula containing 10-fold dose of the modified live virus (MLV) component to non-vaccinated and vaccinated pregnant cattle. Study animals consisted of 20 non-vaccinated (Treatment Group T1) an 59 previously vaccinated (Treatment Groups T2=14, T3=15, T4=15, and T5=15) crossbred beef heifers ranging from approximately 160 to 220 days of pregnancy. Pre-breeding vaccination history for the vaccinated animals consisted of a dose of Bovine Rhinotracheitis-Virus Diarrhea-Parainfluenza$_3$-Respiratory Syncytial Modified-Live Virus Vaccine (Bovi-Shield® 4) that was administered to each T3 and T5 animal approximately 150 days prior to breeding and all T2, T3, T4, and T5 animals received a dose of Bovine Rhinotracheitis-Virus Diarrhea-Parainfluenza$_3$-Respiratory Syncytial Modified-Live Virus Vaccine/Campylobacter Fetus-Leptospira Canicola-Grippotyphosa-Hardjo-Icterohemorrhagiae-Pomona Bacterin (PregGuard® 10) approximately 30 days prior to breeding.

On Day 0, each of the 79 pregnant study animals were given an intramuscular does of a Bovi-Shield® 4+L5 formula containing 10 doses of the MLV components. Study animals were observed daily for health status and abortions through parturition, serologic responses to vaccination were determined, diagnostic testing was conducted on abortion cases, and the health and serologic status was determined for each calf. Overall, 15 pregnancies in T1 were affected by vaccination on Day 0 as evidenced by abortions (6) or calves born with pre-nursing neutralizing antibodies to BVDV (9). Abortions attributed to IBRV infection occurred between Day 25 to Day 43 in 6 of the 11 (55%) T1 heifers that were negative (2) for IBRV neutralizing antibodies on Day 0. The remaining T1 heifers (14) delivered healthy calves; however, calves born with BVDV neutralizing antibodies demonstrated that in utero exposure occurred in 9 of 12 (75%) heifers that were negative for BVDV neutralizing antibodies on Day 0.

In comparison, there were no adverse effects on the pregnancies of the previously vaccinated animals in T2, T3, T4, and T5. All (59/59) of these animals delivered healthy calves and 58 (one calf nursed prior to sample collection) of the calves were negative for neutralizing antibodies to IBRV and BVDV.

The pregnancies of heifers that were vaccinated prior to breeding with Bovi-Shield® vaccines were not adversely affected by the administration of a test vaccine formula containing 10 doses of MLV components, demonstrating the safety of these components in vaccinated pregnant cattle.

Study Design:

| Trt. No. | Pre-Study Viral Vaccination History* | | Number of Animals | BOVI-SHIELD 4 + L.5 Vaccination | |
|---|---|---|---|---|---|
| | ~150 Days Prior to Breeding | ~30 Days Prior to Breeding | | Day | IM Doses* |
| T1 | None | None | 20 | 0 | 1 |
| T2 | None | Preg-Guard 10 | 14 | 0 | 1 |
| T3 | Bovi-Shield 4 | Preg-Guard 10 | 15 | 0 | 1 |
| T4 | None | Preg-Guard 10 | 15 | 0 | 1 |
| T5 | Bovi-Shield 4 | Preg-Guard 10 | 15 | 0 | 1 |

*Each 2-ml IM (intramuscular) dose was formulated to contain 10-doses of the MLV components.

Procedures:

Pre-Treatment Phase:

Animals were selected for this study based to minimize the calving interval. Pregnant animals with no history of vaccination for IBRV and BVDV were assigned to Treatment Group T1. Animals were assigned to treatment groups using a completely random design. In summary, these animals had no history of vaccination for IBRV and BVDV, were negative for BVDV, and had serum neutralizing antibody titers of <4 to IBRV and, types 1 and 2 BVDV prior to vaccination. At approximately 150 days prior to breeding, a dose of Bovi-Shield 4 (Bovine Rhinotracheitis-VirusDiarrhea-Parainfluenza$_3$-Respiratory Syncytial Modified-Live Virus Vaccine) was administered to T3 and T5 animals, respectively. At approximately 30 days prior to breeding, a dose of Preg-Guard 10 was administered to each animal in T2 and T3, and T4 and T5, respectively. The vaccines in this study contained 3 7 log$_{10}$ TCID$_{50}$ per 2-ml dose of IBRV and 2.7 log$_{10}$ TCID$_{50}$ per 2-ml dose of BVD.

Treatment Phase:

Beginning on Day-1, all animals were observed daily for general health status and abortions through parturition. On Day 0, each animal's pregnancy status was confirmed and two serum separation tubes (SSTs) of blood were collected from each animal. The Bovi-Shield 4+L5 vaccine was prepared and a 2-ml IM dose containing 10-doses of the vaccine's four MLV components were administered to each of the 79 study animals. All animals were observed for adverse reactions for approximately one hour following vaccination.

All aborting animals were identified and two SST blood samples (acute) were collected, processed to serum, labeled, and stored frozen. Aborted fetus samples, available for five of the six abortions were shipped to a diagnostic lab. Approximately two weeks later, two additional SST blood samples (convalescent) were collected from the dams, processed to serum, labeled, and stored frozen.

Parturition Phase:

On the day of calving, each calf's health and nursing status was determined, and a blood sample (2-SSTs) was collected from each calf. A post-nursing blood sample (2-SSTs) was collected from each calf at three days of age. Blood samples collected from the calves were processed to serum, labeled, stored frozen, and tested.

Serum Testing:

The sera obtained from the heifers and the calves were tested for neutralizing antibodies to IBRV, and types 1 and 2 BVDV. The total serum IgG concentration was also determined on pre- and post-nursing sera if the calf was not observed to have nursed prior to sample collection, and its pre-nursing sera tested positive ($\geqq 4$) for neutralizing antibodies to IBRV and/or BVDV.

Results:

TABLE 1: Test Vaccine Modified Live Virus Components

TABLE 2: Day 0 and Day 28 Geometric Mean and Range of IBRV Neutralizing Antibodies Titers TABLE 3: Day 0 and Day 28 Geometric Mean and Range of Type 1 BVDV Neutralizing Antibody Titers TABLE 4: Day 0 and Day 28 Geometric Mean and Range of Type 2 BVDV Neutralizing Antibody Titers TABLE 5: Summary of Effects on Pregnancy Attributed to Day 0 Treatment TABLE 6: Summary of Individual Results for Treatment Group T1

Test Vaccine Modified Live Virus Components:

As summarized in Table 1, the Bovi-Shield 4+L5 formula administered to each study animal on Day 0 contained 7.0, 5.5, 7.5, and 5.7 log$_{10}$ TCID$_{50}$ of the vaccine's modified live IBRV, BVDV, PIB3, and BRSV components, respectively.

Serologic Responses to Vaccination:

Tables 2, 3, and 4 contains each treatment group's pre-(Day 0) and post-vaccination (Day 28) geometric mean and range of serum neutralizing antibody titers to IBRV, type 1 BVDV, and type 2 BVDV, respectively.

The pre-vaccination mean IBRV antibody titer for the non-vaccinated (T1) animals was 2, and 11/20 T1 animals were negative (<2) for neutralizing antibodies to IBRV. Pre-vaccination mean IBRV antibody titers (14, 16, 16, and 21) for the vaccinated animals (T2, T3, T4, and T5) were similar regardless of pre-breeding vaccination regimen (one or two doses) and formula (minimum immunizing or release levels of IBRV components). Mean antibody titers for T1, T2, T3, T4, and T5 increased substantially in response to vaccination with Day 28 means of 86, 130, 94, 106, and 97, respectively. Nineteen of the 20 non-vaccinated (T1) animals were negative for both type 1 and type 2 BVDV antibodies on Day 0. Vaccinate (T2, T3, T4, and T5) mean type 1 (223, 215, 315, and 250) and type 2 (44, 57, 84, and 58) BVDV neutralizing antibody titers were similar regardless of pre-breeding vaccination regimen and formula. By Day 28, T1 mean titers to type 1 (181) and type 2 (15) BVDV were markedly increased while T2, T3, T4, and T5 mean titers to type 1 (208, 228, 277, and 231) and type 2 BVDV (49, 63, 58, and 58) remained comparable to pre-vaccination levels.

Effects of Day 0 Treatment of Pregnancy:

The effects of Day 0 treatment (vaccination) on the pregnancies of each treatment group are summarized in Table 5. Overall, 15 of the T1 pregnancies were affected by vaccination as evidenced by abortions (6) or calves born with pre-nursing neutralizing antibodies to BVDV (9). In comparison, there were no adverse effects on the pregnancies of the previously vaccinated animals in T2, T3, T4, and T5. All (59/59) of these animals delivered healthy calves and 58 (one calf nursed prior to sample collection) of the calves were negative for neutralizing antibodies to IBRV and BVDV.

Summary of Individual Results for Treatment Group T1:

Individual abortion and calving results for the non-vaccinated animals (T1) are summarized in Table 6. Abortions attributed to IBRV infection occurred between Day 25 and Day 43 in 6 of the 11 (55%) T1 heifers that were negative (<2) for IBRV neutralizing antibodies on Day 0. The remaining T1 heifers (14) delivered healthy calves; however, calves born with BVDV neutralizing antibodies demonstrated that in-utero exposure occurred in 9 of 12 (75%) heifers that were negative for BVDV neutralizing on Day 0.

CONCLUSION

The pregnancies of heifers that were vaccinated prior to breeding with BOVI-SHIELD® vaccines were not adversely affected by the administration of a test vaccine formula containing 10 field doses of BOVI-SHIELD®'s MLV components, demonstrating the safety of these viruses in vaccinated pregnant cattle.

TABLE 1

Test Vaccine Modified Live Virus Components

| BOVI-SHIELD 4 + L5 | $Log_{10}TCID_{50}$ per 2-ml Dose | | | |
| --- | --- | --- | --- | --- |
| | IBRV | BVDV | $PIV_3$ | BRSV |
| Test Vaccine Formula* | 7.0 | 5.5 | 7.5 | 5.7 |

*Each study animal received an additional $1.0 log_{10}TCID_{50}$ of each viral component as each 2-ml dose of test vaccine was formulated to contain 10-doses of the modified live virus components.

TABLE 2

Day 0 and Day 28 Geometric Mean and Range of IBRV Neutralizing Antibody Titers

| Trt. Gp. | Number of Pre-Breeding Vaccinations | Number of Animals | Day 0 GMT** | Day 28 GMT** | Day 0 Titer Range | Day 28 Titer Range |
| --- | --- | --- | --- | --- | --- | --- |
| T1 | 0 (Not Applicable) | 20 | 2 | 86 | ***<2-16 | 16-304 |
| T2 | 1 (IBRV) | 14 | 14 | 130 | 7-91 | 54-431 |
| T3 | 2 (IBRV) | 15 | 16 | 94 | 10-27 | 38-128 |
| T4 | 1 (BVDV) | 15 | 16 | 106 | 5-181 | 27-304 |
| T5 | 2 (BVDV) | 15 | 21 | 97 | 8-152 | 27-431 |

**Titers of <2 were calculated as 1.0 prior to $log_2$ transformation for determining GMT (geometric mean titer).
***Eleven of 20 T1 animals were negative (<2) for neutralizing antibodies to IBRV.

TABLE 3

Day 0 and Day 28 Geometric Mean and Range of Type 1 BVDV Neutralizing Antibody Titers

| Trt. Gp. | Number of Pre-Breeding Vaccinations | Number of Animals | Day 0 GMT** | Day 28 GMT** | Day 0 Titer Range | Day 28 Titer Range |
| --- | --- | --- | --- | --- | --- | --- |
| T1 | 0 (Not Applicable) | 20 | 1 | 181 | ***<2-1218 | 32-1218 |
| T2 | 1 (IBRV) | 14 | 223 | 208 | 76-1024 | 54-724 |
| T3 | 2 (IBRV) | 15 | 215 | 228 | 38-861 | 91-512 |
| T4 | 1 (BVDV) | 15 | 315 | 277 | 76-861 | 45-724 |
| T5 | 2 (BVDV) | 15 | 250 | 231 | 64-861 | 64-861 |

**Titers of <2 were calculated as 1.0 prior to $log_2$ transformation for determining GMT (geometric mean titer).
***Nineteen of 20 T1 animals were negative for neutralizing antibodies to type 1 BVDV.

TABLE 4

Day 0 and Day 28 Geometric Mean and Range of Type 2 BVDV Neutralizing Antibody Titers

| Trt. Gp. | Number of Pre-Breeding Vaccinations | Number of Animals | Day 0 GMT** | Day 28 GMT** | Day 0 Titer Range | Day 28 Titer Range |
| --- | --- | --- | --- | --- | --- | --- |
| T1 | 0 (Not Applicable) | 20 | 1 | 15 | ***<2-609 | 3-362 |
| T2 | 1 (IBRV) | 14 | 44 | 49 | 8-256 | 13-181 |
| T3 | 2 (IBRV) | 15 | 57 | 63 | 4-215 | 23-128 |

TABLE 4-continued

Day 0 and Day 28 Geometric Mean and Range of Type 2 BVDV Neutralizing Antibody Titers

| Trt. Gp. | Number of Pre-Breeding Vaccinations | Number of Animals | Day 0 GMT** | Day 28 GMT** | Day 0 Titer Range | Day 28 Titer Range |
|---|---|---|---|---|---|---|
| T4 | 1 (BVDV) | 15 | 84 | 58 | 27-431 | 13-181 |
| T5 | 2 (BVDV) | 15 | 58 | 58 | 13-181 | 16-181 |

**Titers of <2 were calculated as 1.0 prior to $\log_2$ transformation for determining GMT (geometric mean titer).
***Nineteen of 20 T1 animals were negative for neutralizing antibodies to type 2 BVDV.

TABLE 5

Summary of Effects on Pregnancy Attributed to Day 0 Treatment

| Trt. Gp. | Number of Pre-Breeding Vaccinations | Number of Animals | Number of Abortions | Number of Healthy Calves** | Number of Calves Positive for Pre-Nursing VN Antibodies** | | | Number of Pregnancies Affected by Day 0 Treatment |
|---|---|---|---|---|---|---|---|---|
| | | | | | IBRV | BVDV-1 | BVDV-2 | |
| T1 | 0 (Not Applicable) | 20 | 6 | 14 | 0 | 9 | 7 | 15 |
| T2 | 1 (IBRV) | 14 | 0 | 14 | 0 | 0 | 0 | 0 |
| T3 | 2 (IBRV) | 15 | 0 | 15 | 0 | 0 | 0 | 0 |
| T4 | 1 (BVDV) | 15 | 0 | 15 | 0 | 0 | 0 | 0 |
| T5 | 2 (BVDV) | 15 | 0 | 15 | 0 | 0 | 0 | 0 |
| Vaccinate (T2, T3, T4 & T5) Total: | | 59 | 0 | 59 | 0 | 0 | 0 | 0 |

**All calves were born between Day 47 and Day 123. Abortions occurred between Day 25 and Day 43.
***Pre-nursing blood samples were not obtained from one calf in T1 (#315) and T4 (#92). T1 calves with pre-nursing antibodies had titers of ≧23 for BVDV-1 (type 1 BVDV) and ≧19 for BVDV-2 (type 2 BVDV). All 58 pre-nursing serum samples collected from the T2, T3, T4, and T5 calves were negative (<2) for neutralizing antibodies.

TABLE 6

Summary of Individual Results for Treatment Group T1

| T1 Heifer No. | Day 0 Serum Neutralizing Antibody Titer | | | Day Aborted or Delivered Healthy Calf | Calf Pre-and Post-Nursing Serum Neutralizing Antibody Titers | | | | | |
|---|---|---|---|---|---|---|---|---|---|---|
| | IBRV | BVDV-1 | BVDV-2 | | Pre-Nurse IBRV | Post-Nurse IBRV | Pre-Nurse BVDV-1 | Post-Nurse BVDV-1 | Pre-Nurse BVDV-2 | Post-Nurse BVDV-2 |
| 316 | <2 | <2 | <2 | Aborted on Day 25 | — | — | — | — | — | — |
| 48 | <2 | <2 | <2 | Aborted on Day 27 | — | — | — | — | — | — |
| 213 | <2 | <2 | <2 | Aborted on Day 28 | — | — | — | — | — | — |
| 205 | <2 | <2 | <2 | Aborted on Day 34 | — | — | — | — | — | — |
| 258 | <2 | <2 | <2 | Aborted on Day 34 | — | — | — | — | — | — |
| 202 | <2 | <2 | <2 | Aborted on Day 43 | — | — | — | — | — | — |
| 313 | <2 | 1218 | 609 | Healthy calf | <2 | 8 | <2 | 609 | <2 | >362 |
| 244 | <2 | <2 | <2 | Healthy calf | <2 | 6 | 76 | 304 | 2 | 32 |
| 312 | <2 | <2 | <2 | Healthy calf | <2 | 13 | 23 | 1218 | <2 | 64 |
| 314 | <2 | <2 | <2 | Healthy calf | <2 | 23 | 431 | 1218 | 27 | 304 |
| 17 | 4 | <2 | <2 | Healthy calf | <2 | 54 | 2048 | 3444 | 256 | 304 |
| 73 | 4 | <2 | <2 | Healthy calf | <2 | 45 | 152 | 304 | 152 | 861 |

TABLE 6-continued

Summary of Individual Results for Treatment Group T1

| T1 Heifer No. | Day 0 Serum Neutralizing Antibody Titer | | | Day Aborted or Delivered | Calf Pre-and Post-Nursing Serum Neutralizing Antibody Titers | | | | | |
|---|---|---|---|---|---|---|---|---|---|---|
| | IBRV | BVDV-1 | BVDV-2 | Healthy Calf | Pre-Nurse IBRV | Post-Nurse IBRV | Pre-Nurse BVDV-1 | Post-Nurse BVDV-1 | Pre-Nurse BVDV-2 | Post-Nurse BVDV-2 |
| 135 | 11 | <2 | <2 | Healthy calf | <2 | 38 | 431 | 1024 | 23 | 108 |
| 143 | 13 | <2 | <2 | Healthy calf | <2 | 64 | 609 | 2048 | 54 | 152 |
| 176 | 2 | <2 | <2 | Healthy calf | <2 | 32 | 256 | 512 | 54 | 128 |
| 177 | 6 | <2 | <2 | Healthy calf | <2 | 32 | 54 | 362 | 19 | 45 |
| 315 | <2 | <2 | <2 | Healthy calf | (45) | 108 | (16) | 431 | (<2) | 32 |
| 51 | 16 | <2 | <2 | Healthy calf | <2 | 27 | <2 | 431 | <2 | 23 |
| 80 | 5 | <2 | <2 | Healthy calf | <2 | 54 | <2 | 128 | <2 | 16 |
| 167 | 11 | <2 | <2 | Healthy calf | <2 | <2 | <2 | 6 | <2 | 3 |

EXAMPLE 2

A field safety study was conducted to assess the efficacy of the Bovi-Shield® product line. This Example summarizes the interim results through Day 78 of the study. This study compared the safety of administering a Placebo (sterile water diluent) or one of three lots of Bovine Rhinotracheitis-Virus Diarrhea-Parainfluenza$_3$-Respiratory Syncytial Modified-Live Virus Vaccine/Leptospira Canicola-Grippotyphosa-Hardjo-Icterohaemorrhagiae-Pomona Bacterin (Bovi-Shield® FP 4+L5) to first trimester pregnant, crossbred beef cows that were vaccinated prior to breeding with Bovine Rhinotracheitis-Virus Diarrhea-Parainfluenza$_3$, Modified Live Virus-Campylobacter Fetus-Leptospira Canicola-Grippotyphosa-Hardjo-Icterohaemorrhagiae-Pomona Bacterin (PregGuard™ FP 9).

On Day 0, blood samples were collected from each animal, and all animals were examined by ultrasound to confirm pregnancy status. On Day 0, an intramuscular (IM) dose of Placebo was administered to each of the 304 control animals that were randomly allocated to Treatment Group T1. Each of the 303 animals allotted to the three vaccine treatment groups T2 (n=106), T3 (n=101), and T4 (n=96) received an IM dose of their assigned lot of Bovi-Shield® FP 4+L5. There were no observations of adverse local or systemic reactions following vaccination. The animals were observed weekly for health status. One of 302 control cows (T1) was open, and all cows that were vaccinated with Bovi-Shield FP 4+L5 [T2(n=102), T3 (n=100), and T4 (n=95)] were confirmed pregnant. The abortion rates were very similar for the control (T1) and vaccinated (T2 through T4) animals, 0.3% versus 0.0%, respectively. The serological testing results from the open T1 cow (#286) indicated that there were no substantial changes in titers from Day 0 for any of the fractions.

The results of this field safety study demonstrated that previously vaccinated, approximately first trimester pregnant animals that were administered Bovi-Shield® FP 4+L5 vaccine had abortion rates through Day 78 that were not higher than animals that were administered a Placebo supporting the safety of these vaccine components in vaccinated, pregnant animals.

Study Design:

| Trt. No. | Treatment Description | Number of Animals | Vaccination | | | Pregnancy Check |
|---|---|---|---|---|---|---|
| | | | Day | Dose | Route | |
| T1 | Sterile Diluent (Placebo) | 304 | 0 | 2 ml | IM | Day 77 |
| T2 | BOVI-SHIELD FP 4 + L5 | 106 | 0 | 2 ml | IM | Day 77 |
| T3 | BOVI-SHIELD FP 4 + L5 | 101 | 0 | 2 ml | IM | Day 77 |
| T4 | BOVI-SHIELD FP 4 + L5 | 96 | 0 | 2 ml | IM | Day 77 |

Treatment Phase:

Animals were observed weekly for general health status. On Day 0, animals were observed for general health status, their pregnancy status was confirmed, and two serum separation tubes (SSTs) of blood were collected from each animal. The Placebo (sterile diluent) and BOVI-SHIELD FP 4+L5 vaccines were prepared, and 1-dose (2-ml) was administered to appropriate animals via the intramuscular (IM) route on the side of the neck. Each animal in Treatment Group T1 received a dose of Placebo while the animals in Treatment Groups T2, T3, and T4 received a dose of their respective lot of BOVI-SHIELD FP 4+L5. Observations for untoward systemic reactions were made for approximately one hour following vaccination. The blood samples were processed to serum, labeled, and stored frozen.

On Day 77, a second pregnancy examination was conducted for all animals. Any animal that was not pregnant (open), was recorded as aborted. Two SST blood samples (acute) were collected from the animal. The samples were processed to serum, labeled, and stored frozen. Approximately two weeks later, two additional SST blood samples (convalescent) were collected from the aborting animal, and the samples were processed to serum, labeled, and stored frozen. Day 0, acute, and convalescent serum samples were shipped to the Veterinary Diagnostic Laboratory for bovine abortion serology evaluation.

Results:

Table 7: Summary of Dose for Modified Live Virus Components and Post-vaccination Reactions Table 8: Summary of Abortion Results by Treatment Table 9: Results of Serological Testing Potency of Test Vaccines and Post-Vaccination Reactions:

The potency of the modified live IBRV, BVDV, $PIV_3$, and BRSV components of each lot of Bovi-Shield FP 4+L5 administered on Day 0 exceeded release requirements as detailed in Table 7. All additional testing required for release for commercial distribution were satisfactory. There were no adverse local or systemic reactions observed following vaccination on Day 0.

that were administered a Placebo supporting the safety of these vaccine components in vaccinated, pregnant animals.

TABLE 7

Summary of Potency for Modified Live Virus Components and Post-vaccination Reactions

| Trt. No. | Day 0 Treatment | $Log_{10}TCID_{50}$ Dose | | | | Post-Vaccination Observations for Adverse Local or Systemic Reactions |
|---|---|---|---|---|---|---|
| | | IBRV | BVDV | $PIV_3$ | BRSV | |
| T1 | Sterile Diluent | — | — | — | — | 0/304 |
| T2 | Bovi-4 + L5 | 6.0 | 4.2 | 6.5 | 4.8 | 0/106 |
| T3 | Bovi-4 + L5 | 6.0 | 4.2 | 6.7 | 5.0 | 0/101 |
| T4 | Bovi-4 + L5 | 6.0 | 4.5 | 6.5 | 4.7 | 0/96 |

TABLE 8

Summary of Abortion Results by Treatment

| Treatment Group | Number of Animals | Number of Abortions (Rate) | Etiology (Number) | | | |
|---|---|---|---|---|---|---|
| | | | IBRV Infection | BVD Infection | Congenital Defects | Unknown |
| T1 (Controls) | 302 | 1 (0.3%) | 0 | 0 | 0 | 1 |
| T2 through T4 (Vaccinates) | 297 | 0 (0.0%) | 0 | 0 | 0 | 0 |
| T2 | 102 | 0 (0.0%) | 0 | 0 | 0 | 0 |
| T3 | 100 | 0 (0.0%) | 0 | 0 | 0 | 0 |
| T4 | 95 | 0 (0.0%) | 0 | 0 | 0 | 0 |

TABLE 9

Results of Serological Testing

| Trt. Grp. | Day | Leptospiral Fraction | | | | | IBR | BVD | Vibrio |
|---|---|---|---|---|---|---|---|---|---|
| | | Pomona | Canicola | Grippo | Ictero | Hardjo | | | |
| T1 (#286) | 0 | 100-400 | Neg-100 | Neg-400 | Neg-100 | Neg-200 | 16-32 | 4-8 | Neg |
| | 77 | 200 | 100 | 100 | 100 | Neg | 16 | 8 | Neg |
| | 91 | 200 | 100 | 100 | 100 | Neg | 32 | 8 | Neg |

Summary of Abortion Results:

As summarized in Table 8, the abortion data collected through Day 77 were similar for the control and vaccine treatment groups. Only one of the 303 (0.3%) control animals (T1) and none of the 297 (0.0%) vaccinated animals (T2 through T4) aborted during the study.

The results of the serological testing for the control cow (T1) that aborted (Animal Number 286) are presented in Table 9.

CONCLUSION

The results of this field safety study demonstrated that previously vaccinated, first trimester pregnant animals that were administered Bovi-Shield® FP 4+L5 vaccine had abortion rates through Day 78 that were not higher than animals

EXAMPLE 3

A field safety study was conducted for the Bovi-Shield® product line. This study compared the safety of administering a Placebo (sterile water diluent) or one of three lots of Bovine Rhinotracheitis-Virus Diarrhea-Parainfluenza$_3$-Respiratory Syncytial Modified-Live Virus Vaccine/Leptospira Canicola-Grippotyphosa-Hardjo-Icterohaemorrhagiae-Pomona Bacterin (Bovi-Shield® 4+L5) to second trimester pregnant, Holstein heifers that were vaccinated prior to breeding with Bovi-Shield® 4+L5. On Day-1, blood samples were collected from each animal, and all animals were examined by rectal palpation to confirm pregnancy status. On Day 0, an intramuscular (IM) dose of Placebo was administered to each of the 238 control animals that were randomly allocated to Treatment Group T1. Each of the 237 animals allotted to the three vaccine treatment groups T2 (n=80), T3 (n=79), and T4 (n=78) received an IM dose of their assigned lot of Bovi-Shield® 4+L5. Each lot of vaccine met all testing requirements for release and commercial distribution. There were no observations of adverse local or systemic reactions following vaccination. The animals were observed daily for health status through parturition and the health condition of each newborn calf was determined. Four animals were removed from the study, two (1-T1 and 1-T2) were injured and two (1-T1 and 1-T4) had incorrect breeding dates. Aborting animals were identified, available fetus and placenta samples, and pre-vaccination (Day-1), acute, and convalescent sera were tested to determine possible causes of the abortions. Abortion and normal calving rates were very similar for the control (T1) and vaccinated (T2 through T4) animals. Eleven of the 236 (4.7%) control animals and 14 of the 235 (6.0%) vaccinated (T2 through T4) animals aborted during the study. One (T4) of the 25 abortions was attributed to IBRV infection. The etiologies for the remaining 24 abortion cases were Neospora infections, congenital defects, and unknown causes that occurred in 9 (T1=3, T2=1, T3=1, and T4=4), 1 (T1), and 14 (T1=7, T2=5, and T3=2) animals, respectively. The overall normal calving rates, consisting of the percentage of dams that delivered healthy live calves and normal calves that died during parturition, were 95.3% (225/236) for the control (T1) group and 93.6% (220/235) for the vaccinate (T2 through T4) groups.

The results of this field safety study demonstrated that previously vaccinated, approximately second trimester pregnant animals that were administered a Placebo or Bovi-Shield® 4+L5 vaccine had similar abortion and normal calving rates supporting the safety of these vaccine components in vaccinated, pregnant animals.

Study Design:

to serum, labeled, and stored frozen. The animals were also evaluated daily for general health status and abortions on Day-1 through parturition.

Treatment Phase:

On Day 0, Placebo and Bovi-Shield 4+L5 vaccines were prepared and administered to appropriate animals via the intramuscular (IM) route on the side of the neck. Each T1 animal received a dose of Placebo (sterile water diluent). Each T2, T3, and T4 animal was given a dose of BOVI-SHIELD 4+L5. Observations for adverse systemic reactions were made for approximately one hour following vaccination.

Animals were observed daily for general health status and abortions through parturition. Aborting animals were identified, and two SST blood samples (acute) were collected, processed to serum, labeled, and stored frozen. Available aborted fetus and placenta samples were tested to attempt to determine possible causes of the abortions. Approximately 2 weeks after the abortion, two additional SST blood samples (convalescent) were collected from the aborting animal, and samples were processed to serum, labeled, and stored frozen.

Parturition Phase:

The health status of each calf was determined. All calf mortalities were also assessed to determine the cause of death except for three dystocia related mortalities and all fetotomies.

Results:

Table 10: Summary of Modified Live Virus Components and Post-Vaccination Reactions Table 11: Summary of Abortion Results by Treatment Table 12: Summary of Calving Results by Treatment Test Vaccines and Post-Vaccination Reactions:

The modified live IBRV, BVDV, $PIV_3$, and BRSV components of each lot of Bovi-Shield 4+L5 administered on Day 0

| Trt. No. | Pre-Breeding Vaccination History | Number of Animals | Pregnancy Status and Serum Sample Collection Day | One Intramuscular Dose Administered at Second Trimester of Pregnancy | | Post-Vaccination Monitoring |
|---|---|---|---|---|---|---|
| | | | | Day | Treatment Description | |
| T1 | Bovi-Shield 4 + L5 | 238 | −1 | 0 | Sterile Diluent (Placebo) | Daily observations for health status and abortions. Newborn calf health status. |
| T2 | Bovi-Shield 4 + L5 | 80 | −1 | 0 | Bovi-Shield 4 + L5 | |
| T3 | Bovi-Shield 4 + L5 | 79 | −1 | 0 | Bovi-Shield 4 + L5 | |
| T4 | Bovi-Shield 4 + L5 | 78 | −1 | 0 | Bovi-Shield 4 + L5 | |

Procedures:

Pre-Treatment Phase:

Breeding dates for healthy, crossbred dairy heifers with a pre-breeding history of Bovi-Shield 4+L5 vaccination were provided prior to the start of the study. Animals were assigned to treatments completely at random. On Day-1, two serum separation tubes (SSTs) of blood were collected from each animal, and all animals were examined by rectal palpation to confirm pregnancy status. The blood samples were processed are detailed in Table 10. All additional testing required for release for commercial distribution were satisfactory. There were no adverse local or systemic reactions observed following vaccination on Day 0.

Summary of Abortion Results:

As summarized in Table 11, abortion results were similar for the control and vaccine treatment groups. Eleven of the 236 (4.7%) control (T1) animals and 14 of the 235 (6.0%) vaccinated (T2 through T4) animals aborted during the study.

One (T4) of the 25 abortions was attributed to IBRV. The remaining 24 abortions were attributed to Neospora, congenital defects, and unknown causes, and occurred in 9 (T1=3, T2=1, T3=1, and T4=4), 1 (T1), and 14 (T1=7, T2=5, and T3=2) animals, respectively.

Summary of Calving Results:

The calving results for each treatment group are listed in Table 12. The overall normal calving rates, consisting of the percentage of dams that delivered healthy live calves and normal calves that died during parturition, were 95.3% (225/236) for the control (T1) and 93.6% (220/235) for the vaccinate (T2 through T4) groups. Within the control (T1) group, 79.7% of the calves were alive and healthy while 20.3% died during parturition. In comparison, 78.4% of the calves delivered by vaccinated animals (T2 through T4) were alive and healthy, and 21.20% of their calves died during the birthing process. One T4 animal delivered a dead calf that was attributed to infection with Neospora.

CONCLUSION

The results of this field safety study demonstrated that previously vaccinated, second trimester pregnant animals that were administered a Placebo or Bovi-Shield® 4+L5 vaccine had similar abortion and normal calving rates supporting the safety of these vaccine components in vaccinated, pregnant animals.

TABLE 12

Summary of Calving Results by Treatment

| Treatment Group | Normal Calving Rates* (Animals Delivering Normal Calves/Total Number of Animals) | Normal Calves** | |
|---|---|---|---|
| | | Live Healthy Calf Rates | Dystocia Mortality Rates |
| T1 (Controls) | 95.3% (225/236) | 79.7% | 20.3% |
| T2 through T4 (Vaccinates) | 93.6% (220/235) | 78.4% | 21.2%*** |
| T2 | 92.4% (73/79) | 83.6% | 16.4% |
| T3 | 96.2% (76/79) | 76.6% | 23.4% |
| T4 | 92.2% (71/77) | 75.0% | 23.6%*** |

*Dam determined to have a normal calf if the calf was alive and healthy, or the calf was determined to be normal but death was due to dystocia.
**Rates includes two sets of twins for T1 and one set of twins for T3.
***Mortality for one abnormal calf in T4 was attributed to Neospora infection.

EXAMPLE 4

A field safety study was conducted, comparing the safety of administering a Placebo (sterile water diluent) or one of three lots of Bovine Rhinotracheitis-Virus Diarrhea-Parainfluenza$_3$-Respiratory Syncytial Modified-Live Virus Vaccine/Leptospira Canicola-Grippotyphosa-Hardjo-Icterohaemor-

TABLE 10

Summary of Potency for Modified Live Virus Components and Post-Vaccination Reactions

| Trt. Grp. | Day 0 Treatment* | Log$_{10}$TCID$_{50}$ Dose | | | | Post-Vaccination Observations for Adverse Local or Systemic Reactions |
|---|---|---|---|---|---|---|
| | | IBRV | BVDV | PIV$_3$ | BRSV | |
| T1 | Sterile Diluent | — | — | — | — | 0/238** |
| T2 | Bovi-4 + L5 | 6.0 | 4.2 | 6.5 | 4.8 | 0/80** |
| T3 | Bovi-4 + L5 | 6.0 | 4.2 | 6.7 | 5.0 | 0/79 |
| T4 | Bovi-4 + L5 | 6.0 | 4.5 | 6.5 | 4.7 | 0/78** |

*The lots of Bovi-4 (Bovi-Shield 4) + L5 listed above met all testing requirements for release and commercial distribution.
**Animal #30075 (T2) and Animal #30400 (T1) were removed from the study due to injuries on Day 110 and Day 181, respectively. Animal #19642 (T4) and Animal #30064 (T1) were removed from the study on Day 238 due to incorrect breeding dates. The data for these four animals were excluded from all summaries and analyses.

TABLE 11

Summary of Abortion Results by Treatment

| Treatment Group | Number of Animals | Number of Abortions (Rate) | Etiology(Number) | | | |
|---|---|---|---|---|---|---|
| | | | IBRV | Neospora Infection | Congenital Defects | Unknown |
| T1 (Controls) | 236 | 11 (4.7%) | 0 | 3 | 1 | 7 |
| T2 through T4 (Vaccinates) | 235 | 14 (6.0%) | 1 | 6 | 0 | 7 |
| T2 | 79 | 6 (7.6%) | 0 | 1 | 0 | 5 |
| T3 | 79 | 3 (3.8%) | 0 | 1 | 0 | 2 |
| T4 | 77 | 5 (6.5%) | 1 | 4 | 0 | 0 | rhagiae-Pomona Bacterin (Bovi-Shield® FP 4+L5) to approximately third trimester pregnant, crossbred beef cattle that were vaccinated prior to breeding with a Bovine Rhinotracheitis-Virus Diarrhea-Parainfluenza$_3$, Vaccine, Modified-Live Virus, Campylobacter Fetus-Leptospira Canicola-Grippotyphosa-Hardjo-Icterohaemorrhagiae-Pomona Bacterin (PregGuard™ FP 9).

Blood samples were collected from each animal, and all animals were examined by rectal palpation to confirm pregnancy status prior to vaccination on Day 0. A 2-ml intramuscular (IM) dose of sterile diluent (placebo) was administered to each of the 150 control animals that were randomly allocated to Treatment Group T1. Each of the 198 animals allotted to the three vaccine treatment groups T2 (n=66), T3 (n=67), and T4 (n=65) received a 2-ml IM dose of their assigned lot of Bovi-Shield® FP 4+L5. Each lot of vaccine met all test requirements for release and commercial distribution. There were no observations of adverse local or systemic reactions following vaccination. The animals were observed for health status through parturition and the health condition of each newborn calf was determined.

The overall normal calving rates, consisting of the percentage of dams that delivered healthy live calves and normal calves that died during parturition (5) or due to adverse weather conditions (1), were 99.3% (148/149) for the control (T1) group and 99.5% (195/196) for the vaccinate (T2 through T4) groups. The results of this field safety study demonstrated that previously vaccinated, approximately third trimester pregnant animals that were administered a Placebo or Bovi-Shield® FP 4+L5 vaccine had similar abortion and normal calving rates supporting the safety of these vaccine components in vaccinated, pregnant animals.

Study Design:

Treatment Phase:

On Day 0, two serum separation tubes (SSTs) of blood were collected from each animal, and all animals were examined by rectal palpation to confirm pregnancy status. The blood samples were processed to serum, labeled, and stored frozen. The Placebo and Bovi-Shield FP 4+L5 vaccines were also prepared and administered to appropriate animals via the intramuscular (IM) route in the right neck area. Each T1 animal received a 2-ml dose of Placebo (sterile diluent). Each T2, T3, and T4 animal was given a 2-ml dose of Bovi-Shield FP 4+L5. Observations for adverse systemic reactions were made for approximately one hour following vaccination.

The animals were observed for general health status and abortions through parturition. Aborting animals were identified, and two SST blood samples (acute) were collected, processed to serum, labeled, and stored frozen. Approximately 2 weeks after the abortion, two additional SST blood samples (convalescent) were collected from the aborting animal, and samples were processed to serum, labeled, and stored frozen.

Parturition Phase:

The health status of each calf was determined. All abnormal calves (mortalities) were attributed to dystocia or adverse weather conditions.

Exclusion/Withdrawal Criteria:

Animal #71 (T1) and Animal #288 (T3) were removed from the study due to injuries that were observed on Day 0 and Day 12, respectively. Animal #237 (T3) delivered a calf on Day 21 but was removed from the study on Day 22 because the calf could not be located to determine its health status. The data for these three animals were excluded from all summaries and analyses.

| Tart. No. | Pre-Breeding Vaccination History | Number of Animals | Pregnancy Status and Serum Sample Collection Day | One Intramuscular Dose Administered to Third Trimester Pregnant Animals | | Post-Vaccination Monitoring |
|---|---|---|---|---|---|---|
| | | | | Day | Treatment Description | |
| T1 | PregGuard FP 9 | 150 | 0 | 0 | Sterile Diluent (Placebo) | Observations for health status and abortions. Newborn calf health status. |
| T2 | PregGuard FP 9 | 66 | 0 | 0 | Bovi-Shield FP 4 + L5 | |
| T3 | PregGuard FP 9 | 67 | 0 | 0 | Bovi-Shield FP 4 + L5 | |
| T4 | PregGuard FP 9 | 65 | 0 | 0 | Bovi-Shield FP 4 + L5 | |

Procedures:

Pre-Treatment Phase:

Breeding dates for healthy, crossbred beef heifers with a pre-breeding history of vaccination with Bovine Rhinotracheitis-Virus Diarrhea-Parainfluenza$_3$, Vaccine, Modified-Live Virus, Campylobacter Fetus-Leptospira Canicola-Grippotyphosa-Hardjo-Icterohaemorrhagiae-Pomona Bacterin (PregGuard™ FP 9) were provided prior to the start of the study. Animals were assigned to treatments completely at random. Post-vaccination, weekly health, and newborn calf health observations were assessed without knowledge of treatment assignments. In addition, laboratory personnel did not have access to treatment group assignments.

Results:

Table 13: Summary of Modified Live Virus Components and Post-Vaccination Reactions Table 14: Summary of Abortion Results by Treatment Table 15: Results of Diagnostic Laboratory Serologic Testing for Abortion Cases Table 16: Summary of Calving Results by Treatment Test Vaccines and Post-Vaccination Reactions:

The titers of the modified live IBRV, BVDV, PIV$_3$, and BRSV components of each lot of Bovi-Shield FP 4+L5 administered on Day 0 are indicated in Table 13. There were no adverse local or systemic reactions observed following vaccination.

Summary of Abortion Results:

As summarized in Table 14, only 1 of the 149 (0.7%) control animals (T1) and 1 of the 196 (0.5%) vaccinated animals (T2 through T4) aborted during the study. Results of diagnostic testing on fetus and/or placenta samples did not determine a cause of these abortions. The results for the diagnostic serology testing for the two abortion cases are presented in Table 15. There were no substantial changes in pre-vaccination, acute, and convalescent levels of serum antibodies to *Leptospira pomona, L. canicola, L. gippotyphosa* (grippo), *L. icterohaemorrhagiae* (ictero), *L. hardjo*, IBRV, and BVDV for either animal.

Summary of Calving Results:

The overall normal calving rates consisting of the percentage of dams that delivered healthy live calves and normal calves that died during parturition are listed in Table 16. The normal calving rates were 99.3% (148/149) for the control (T1) group and 99.5% (195/196) for the vaccinate (T2 through T4) groups. All but six of the normal calves were delivered alive and healthy. Five calves died during the birthing process and one died due to adverse weather conditions.

CONCLUSION

The results of this field safety study demonstrated that previously vaccinated, third trimester pregnant animals that were administered a Placebo or Bovi-Shield® FP 4+L5 vaccine had similar abortion and normal calving rates, supporting the safety of these vaccine components in vaccinated, pregnant animals.

TABLE 13

Summary of Potency for Modified Live Virus Components and Post-Vaccination Reactions

| Trt. Grp. | Day 0 Treatment* | $Log_{10}TCID_{50}$ Dose | | | | Post-Vaccination Observations for Adverse Local or Systemic Reactions |
|---|---|---|---|---|---|---|
| | | IBRV | BVDV | $PIV_3$ | BRSV | |
| T1 | Sterile Diluent | — | — | — | — | 0 |
| T2 | Bovi-Shield 4 (Bovi-4 FP + L5) | 6.0 | 4.2 | 6.5 | 4.8 | 0 |
| T3 | Bovi-Shield 4 (Bovi-4 FP + L5) | 6.0 | 4.2 | 6.7 | 5.0 | 0 |
| T4 | Bovi-Shield 4 (Bovi-4 FP + L5) | 6.0 | 4.5 | 6.5 | 4.7 | 0 |

*The Bovi-Shield 4 modified live virus components listed above and the L5 components for each lot of Bovi-4 (Bovi-Shield 4) FP + L5 listed above met all testing requirements for release and commercial use.

TABLE 14

Summary of Abortion Results by Treatment

| Treatment Group | Number of Animals | Number of Abortions (Rate)* | Etiology |
|---|---|---|---|
| T1 (Controls) | 149 | 1 (0.7%) | Unknown |
| T2 through T4 (Vaccinates) | 196 | 1 (0.5%) | Unknown |

*Animal #332 (T1) and Animal #284 (T3) aborted on Day 26 and Day 13, respectively.

TABLE 15

Results of Diagnostic Laboratory Serologic Testing for Abortion Cases

| Animal (Trt. Gp.) | Sample | Leptospiral Fraction | | | | | BVDV | IBRV |
|---|---|---|---|---|---|---|---|---|
| | | Pomona | Canicola | Grippo | Ictero | Hardjo | | |
| #332 (T1) | Pre-Vaccination Sera | <1:100 | <1:100 | <1:100 | <1:100 | <1:100 | 1:512 | 1:8 |
| | Acute Sera | <1:100 | <1:100 | <1:100 | <1:100 | <1:100 | 1:512 | 1:8 |
| | Convalescent Sera | <1:100 | <1:100 | <1:100 | <1:100 | <1:100 | 1:512 | 1:16 |
| #284 (T3) | Pre-Vaccination Sera | <1:100 | <1:100 | <1:100 | <1:100 | <1:100 | 1:1024 | 1:16 |
| | Acute Sera | 1:100 | 1:800 | 1:100 | 1:100 | <1:100 | 1:512 | 1:32 |
| | Convalescent Sera | 1:400 | <1:100 | 1:100 | 1:100 | <1:100 | 1:512 | 1:32 |

TABLE 16

Summary of Calving Results by Treatment

| Treatment Group | Normal Calving Rates* (Animals Delivering Normal/ Calves/Total Animals) | Normal Calves Live Healthy Calves | Mortality |
|---|---|---|---|
| T1 (Controls) | 99.3% (148/149) | 146 | 2 |
| T2 through T4 (Vaccinates) | 99.5% (195/196) | 192** | 4 |
| T2 | 100.0% (66/66) | 66** | 1 |
| T3 | 98.5% (64/65) | 63 | 1 |
| T4 | 100.0% (65/65) | 63 | 2 |

*Dam determined to have a normal calf if the calf was alive and healthy, or the calf was determined to be normal but died due to dystocia (5) or weather conditions (1).
**One set of twins was delivered by a T2 animal.

What is claimed is:

1. A method of reducing abortions in pregnant animals, wherein said animals are cows or heifers which have been vaccinated prior to pregnancy with a therapeutically effective amount of a first vaccine composition comprising an attenuated Bovine Herpes Virus (BHV-1), said method comprising administering to the pregnant animals a therapeutically effective amount of a second vaccine composition comprising an attenuated live Bovine Herpes Virus (BHV-1).

2. A method of reducing abortions in pregnant animals, wherein said animals are cows or heifers which have been vaccinated prior to pregnancy with a therapeutically effective amount of a first vaccine composition comprising an attenuated Bovine Herpes Virus (BHV-1), said method comprising administering to the pregnant animals a therapeutically effective amount of a second vaccine composition comprising an attenuated live Bovine Herpes Virus (BHV-1) and at least one antigen selected from the group consisting of: Bovine Viral Diarrhea Virus (BVDV); an alt enuated live Parainfluenza Virus Type 3 (PLV3); an attenuated Bovine Respiratory Syncytial Virus (BRSV); Leptospira canicola, Leptospira grippotyphosa, Leptospira borgpetersenii hardjo-prajitno, Leptospira icterohaemorrhagia, Leptospira interrogans pomona, Leptospira borgpetersenii hardjo-bovis, Leptospira bratislava, and Campylobacter fetus.

3. The method of claim 1 or 2, wherein said second vaccine composition further comprises an adjuvant.

4. The method of claim 1 or 2, wherein said second vaccine composition is administered intramuscularly.

5. The method of claim 1 or 2, wherein said second vaccine composition is administered subcutaneously.

6. The method of claim 1 or 2, wherein said second vaccine composition contains from about $10^2$ to about $10^{10}$ TCID$_{50}$ units per dose of each virus.

7. The method of claim 1 or 2, wherein the amount of said second vaccine composition administered is from about 0.1 to about 5.0 ml per dose.

8. The method of claim 1 or 2, wherein the amount of said second vaccine composition administered is about 5 ml per dose.

9. The method of claim 1 or 2, wherein the amount of said second vaccine composition administered is about 2 ml per dose.

* * * * *